(12) United States Patent
Uhlenbrock

(10) Patent No.: US 8,148,580 B2
(45) Date of Patent: Apr. 3, 2012

(54) METHODS OF FORMING A TELLURIUM ALKOXIDE AND METHODS OF FORMING A MIXED HALIDE-ALKOXIDE OF TELLURIUM

(75) Inventor: Stefan Uhlenbrock, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 402 days.

(21) Appl. No.: 12/424,411

(22) Filed: Apr. 15, 2009

(65) Prior Publication Data

US 2010/0267998 A1     Oct. 21, 2010

(51) Int. Cl.
*C07C 31/02* (2006.01)
(52) U.S. Cl. .................................... 568/840; 568/851
(58) Field of Classification Search .............. 568/840, 568/851
See application file for complete search history.

(56) References Cited

U.S. PATENT DOCUMENTS

| | | | |
|---|---|---|---|
| 4,389,389 A | 6/1983 | Badesha | |
| 4,558,026 A | 12/1985 | Brill | |
| 5,164,524 A | 11/1992 | Gedridge, Jr. et al. | |
| 5,442,112 A | 8/1995 | Cole-Hamilton et al. | |

FOREIGN PATENT DOCUMENTS

| | | |
|---|---|---|
| JP | 7268505 | 10/1995 |
| JP | 1995268505 A | 10/1995 |
| WO | WO 2008/057616 | 5/2008 |
| WO | PCT/US2010/028510 | 10/2010 |

OTHER PUBLICATIONS

Hodgson et al., "Sol-Gel Processing of Tellurium Oxide and Suboxide Thin Films with Potential for Optical Data Storage Application", Journal of Sol-Gel Science and Technology 18, 2000, pp. 145-158.
Spangler, "Synthesis and Characterization of Tellurium Isopropoxide", Middle Tennessee State University, Journals, vol. 4, Issue 1, Abstract, Mar. 9, 2009 1 page.
Weng et al., "Achieving controllable sol-gel processing of tellurite glasses through the use of Te(VI) precursors", Abstract, Materials Science and Engineering, vol. 107, Issue 1, Feb. 25, 2004, pp. 89-93.
Mehrotra et al., "Tellurium Alkoxides", Jour. Indian Chem. Soc., vol. 42, No. 1, 1965, 4 pages.

*Primary Examiner* — Sikarl Witherspoon
(74) *Attorney, Agent, or Firm* — Wells St. John, P.S.

(57) ABSTRACT

A method of forming a tellurium alkoxide includes providing a tellurium halide and a non-tellurium alkoxide in a liquid organic solvent. The liquid organic solvent has less moles of alcohol, if any, than moles of tellurium halide in the liquid organic solvent. The tellurium halide and the non-tellurium alkoxide within the liquid organic solvent are reacted to form a reaction product halide and a tellurium alkoxide. The liquid organic solvent is removed from the reaction product halide and the tellurium alkoxide to leave a liquid and/or solid mixture comprising the reaction product halide and the tellurium alkoxide. The mixture is heated effective to gasify the tellurium alkoxide from the reaction product halide. Other implementations are disclosed, including methods of forming a mixed halide-alkoxide of tellurium.

26 Claims, 21 Drawing Sheets

METHODS OF FORMING A TELLURIUM ALKOXIDE AND METHODS OF FORMING A MIXED HALIDE-ALKOXIDE OF TELLURIUM

TECHNICAL FIELD

Embodiments disclosed herein pertain to methods of forming a tellurium alkoxide and to methods of forming a mixed halide-alkoxide of tellurium.

BACKGROUND

Integrated circuit memory may be characterized as being either volatile or non-volatile. Volatile memory must be reprogrammed/rewritten, typically multiple times per second, due to charge dissipation. Non-volatile memory, on the other hand, can maintain any of its programmed states without necessarily requiring periodic refresh. Example volatile memory includes Dynamic Random Access Memory (DRAM). Example non-volatile memory includes Static Random Access Memory (SRAM), Flash Memory, and Phase Change Memory (PCM).

There is a continuing goal in the fabrication of integrated circuitry to make individual devices smaller to increase the density of the circuitry, and thereby either reduce the size of the circuitry or enable more circuitry to be packed into a smaller space. Yet, the smaller and denser circuitry must be reliable in operation. Phase change memory is of increasing interest due to its apparent ability to be scaled smaller and maintain reliability.

The primary components of phase change memory are a pair of electrodes having a phase change material sandwiched there-between. The phase change material is capable of being selectively modified in a manner that changes its electrical resistance between at least high and low resistant states which can be "read" and therefore used as solid-state memory. In phase change memory, electric currents of different magnitudes are selectively passed to the phase change material which changes the resistance of the material very rapidly.

Phase change materials are often formed of a combination or alloy of different metals. One metal of interest is tellurium. Such might be combined, for example, with one or both of germanium and antimony to form a GeTe, SbTe, or GeSbTe material. Chemical vapor deposition (CVD) is one method by which such phase change materials may be deposited over a substrate. For example, different deposition precursors comprising one each of germanium, antimony and tellurium may be provided in desired quantities over a substrate under suitable conditions such that a GeSbTe material is deposited having desired quantities of the respective germanium, antimony and tellurium. Example tellurium precursors include tellurium amides and organometallics such as trisdimethylamino tellurium.

Phase change materials may also be used in fabrication of rewritable media, for example rewritable CDs and DVDs.

While embodiments of the invention were motivated in addressing the above-identified issues, the invention is in no way so limited.

DETAILED DESCRIPTION OF EXAMPLE EMBODIMENTS

Embodiments of the invention encompass methods of forming a phase change material comprising germanium and tellurium, and as might be used in any existing or yet-to-be developed application. For example, such might be used in the fabrication of integrated circuitry or in the fabrication of rewritable media. In some embodiments, phase change material comprising germanium and tellurium is incorporated in a method of forming phase change memory circuitry.

Figure 1:
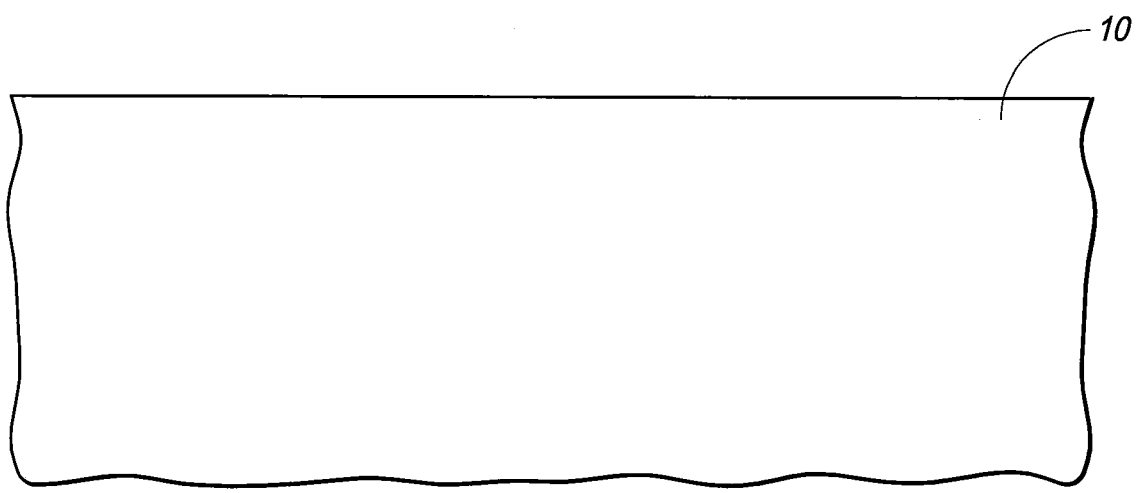
FIG. 1 is a diagrammatic sectional view of a substrate in process in accordance with an embodiment of the invention.

Example embodiments of a method of forming a phase change material comprising germanium and tellurium are initially described with reference to FIGS. 1-5. FIG. 1 depicts a substrate 10 over which a phase change material comprising germanium and tellurium will be deposited. Substrate 10 might comprise any substrate, including semiconductor substrates. In the context of this document, the term "semiconductor substrate" or "semiconductive substrate" is defined to mean any construction comprising semiconductive material, including, but not limited to, bulk semiconductive materials such as a semiconductive wafer (either alone or in assemblies comprising other materials thereon), and semiconductive material layers (either alone or in assemblies comprising other materials). The term "substrate" refers to any supporting structure, including, but not limited to, the semiconductive substrates described above. Substrate 10 may be a suitable substrate to be used in formation of rewritable optical media, for example CDs and DVDs. Regardless, any existing or yet-to-be developed substrate 10 may be used.

Figure 2:
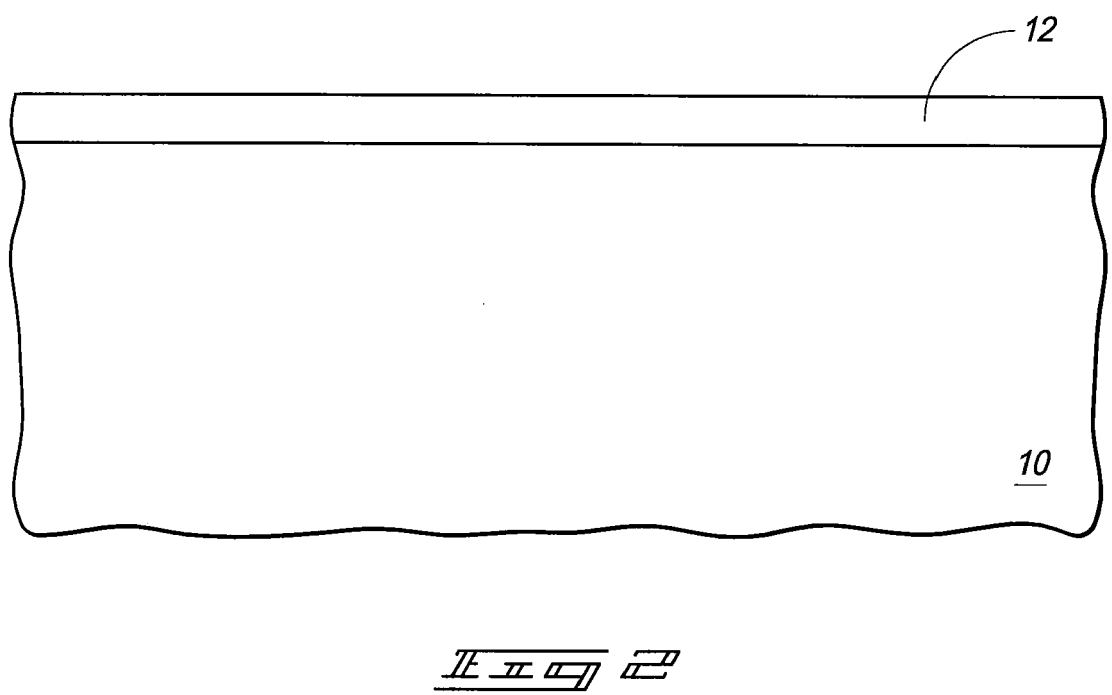
FIG. 2 is a view of the FIG. 1 substrate at a processing step subsequent to that shown by FIG. 1.

Referring to FIG. 2, a germanium-comprising material 20 has been deposited over substrate 10. Such includes at least some germanium in elemental form capable of reacting with tellurium from a tellurium-comprising precursor, as described below. Accordingly, material 12 may comprise, consist, or consist essentially of elemental-form germanium. An example thickness range for material 12 is from 1 Angstrom to 200 Angstroms, and in one embodiment from 1 Angstrom to 20 Angstroms. Material 12 may be deposited by any existing or yet-to-be developed method, including for example physical vapor deposition, chemical vapor deposition, or atomic layer deposition (ALD), including combinations thereof. As an example, elemental germanium may be chemical vapor or atomic layer deposited using a suitable inorganic or organic precursor. An inorganic example is $GeH_4$. Example organic precursors include tetrakis dialkylamido germanium and bis-ditertbutyl germanium amidinate. Example reducing precursors usable to leave an elemental germanium-form monolayer, or in a chemical vapor deposition process, include ammonia, hydrogen, and/or formic acid. Example temperature and pressure ranges include 200° C. to 400° C. and 0.1 mTorr to 10 Torr.

Figure 3:
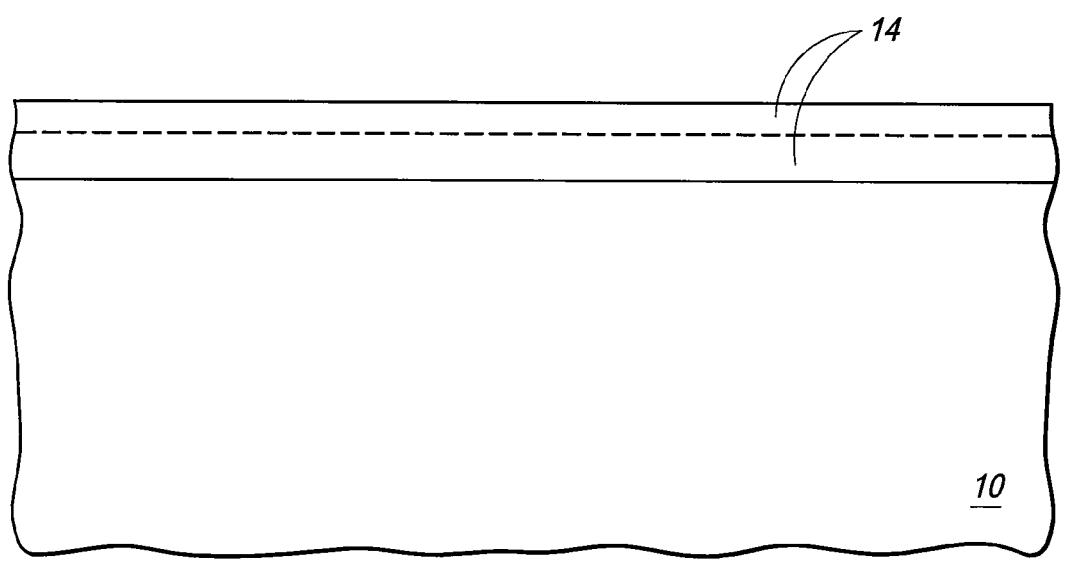
FIG. 3 is a view of the FIG. 2 substrate at a processing step subsequent to that shown by FIG. 2.

Referring to FIG. 3, a gaseous tellurium-comprising precursor has been flowed to the germanium-comprising material 12 of FIG. 2 and tellurium has been removed from the precursor to react with the elemental-form germanium in material 12 (not shown in FIG. 3) to form a germanium and tellurium-comprising compound of a phase change material 14 over substrate 10. Such may form in a chemical vapor deposition manner. For diagrammatic purposes, the dashed line in FIG. 3 depicts the former construction of the FIG. 2 outer surface of the original germanium-comprising material 12.

Phase change material 14 may or may not be homogenous, and the compound which is formed may or may not comprise stoichiometric GeTe ($Ge_1Te_1$). Further, phase change material 14 may comprise one or more additional elements, with antimony being a specific example for formation of a compound comprising germanium, antimony, and tellurium. For example, the germanium-comprising material 12 of FIG. 2 might include one or more additional elements, for example antimony such that material 14 upon formation comprises germanium, antimony and tellurium. As an alternate example, antimony or one or more other metals might be provided within phase change material 14 after its initial formation. Regardless, an example germanium, antimony, and tellurium-comprising material is stoichiometric $Ge_2Sb_2Te_5$, although non-stoichiometric compositions might alternately be formed. In one embodiment, thickness of phase change material 14 formed from flowing the gaseous tellurium-comprising precursor is at least 50% greater in thickness than that of deposited germanium-comprising material 12 of FIG. 2, and in another embodiment at least 100% greater in thickness. FIG. 3 shows ⅔ greater in thickness.

The tellurium-comprising precursor used to form the construction of FIG. 3 from that of FIG. 2 may be organic or inorganic. Additionally, a combination of organic and inorganic tellurium-comprising precursors may be used. Example substrate temperature and chamber pressure ranges include from 200° C. to 450° C., and pressure from 0.1 mTorr to 760 Torr. An example inorganic gaseous tellurium-comprising precursor is $TeH_2$. Example organic gaseous tellurium-comprising precursors include di-tert-butyl telluride, tellurium IV ethoxide, and tetrakis dimethylamido tellurium. In one embodiment, the organic gaseous tellurium-comprising precursor is void of $NR_2$ where R is organic. Regardless, in one embodiment, the tellurium-comprising precursor is void of nitrogen. Substrate temperature during the deposition may be tailored for the specific tellurium-comprising precursor used, for example being a temperature of at least 360° C. for a di-tert-butyl telluride, and at least 260° C. for a tellurium IV ethoxide. Either of such may be flowed to a chamber within which the substrate is received by using a bubbler/vaporizer, or by flowing or spraying a liquid into the chamber under chamber pressure conditions wherein vaporization rapidly occurs.

In one ideal embodiment, formation of the germanium and tellurium-comprising compound of phase change material 14 is chemical vapor deposited in a self-limiting manner. For example, the gaseous tellurium-comprising precursor is fed to the germanium-comprising material until no more of the germanium and tellurium-comprising compound is formed, for example due to no more elemental-form germanium being available within germanium-comprising material 12 of FIG. 2 for reaction, and thereby self-limits in thickness growth. In one embodiment, the flowing of the tellurium-comprising precursor is continued for at least 10 seconds after no more of the compound is formed, for example to assure that reaction has been complete. Some tellurium may be removed in elemental-form from the precursor over phase change material 14 from continued flowing of the gaseous tellurium-comprising precursor to the heated surface of the substrate even after no more the germanium and tellurium-comprising compound is formed.

Figure 4:
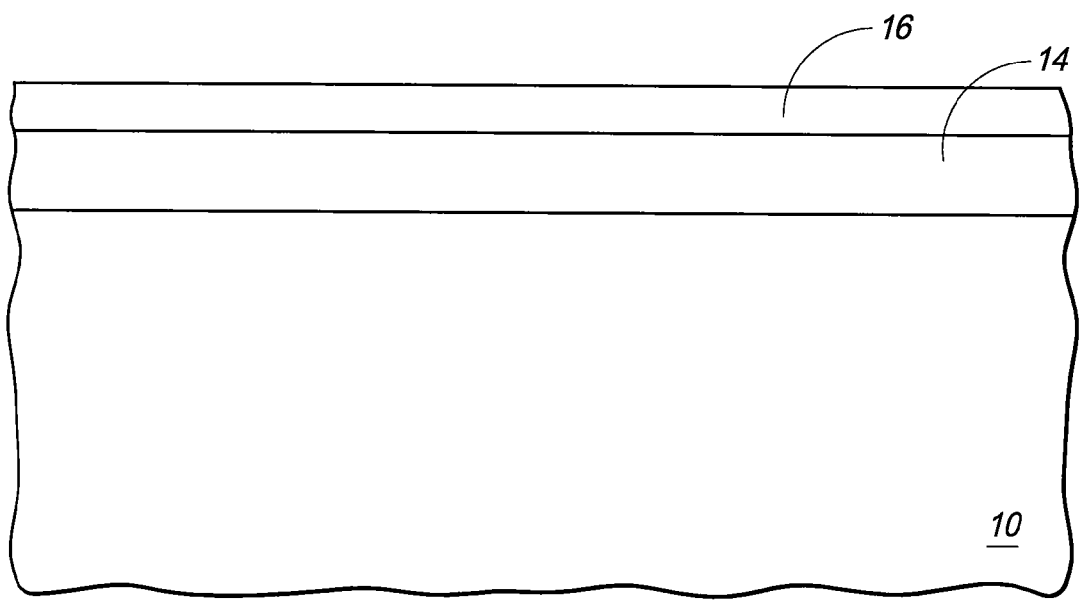
FIG. 4 is a view of the FIG. 3 substrate at a processing step subsequent to that shown by FIG. 3.

The process may be repeated in the same or modified manners one or more times. For example, the processing of FIGS. 2 and 3 may be considered as a cycle. Referring to FIG. 4, more germanium-comprising material 16 which comprises elemental-form germanium has been deposited over phase change material 14. Such may be the same in composition as that of germanium-comprising material 12 or of different composition, and regardless may be deposited in the same or different manner from which material 12 was deposited.

Figure 5:
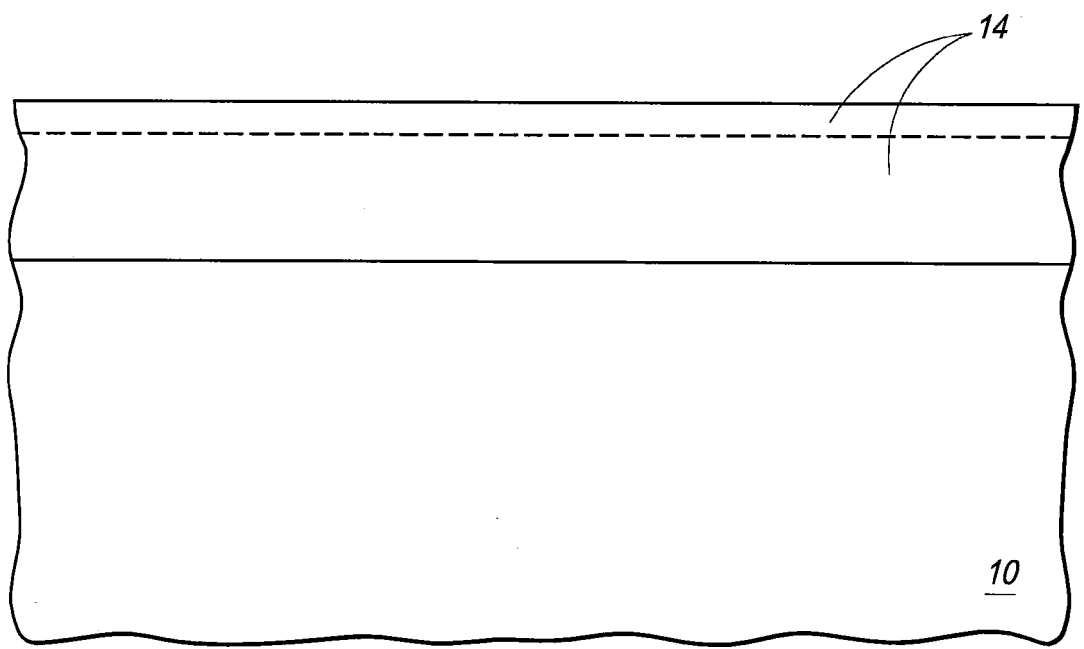
FIG. 5 is a view of the FIG. 4 substrate at a processing step subsequent to that shown by FIG. 4.

Referring to FIG. 5, a gaseous tellurium-comprising precursor has been flowed to the germanium-comprising material of FIG. 4 which removes tellurium to react with the elemental-form germanium to form a germanium and tellurium-comprising compound, for example depicted in FIG. 5 as the continuing growth or deposition of phase change material 14. The former outer surface of germanium-comprising material 16 is shown with a dash line in FIG. 5.

Figure 6:
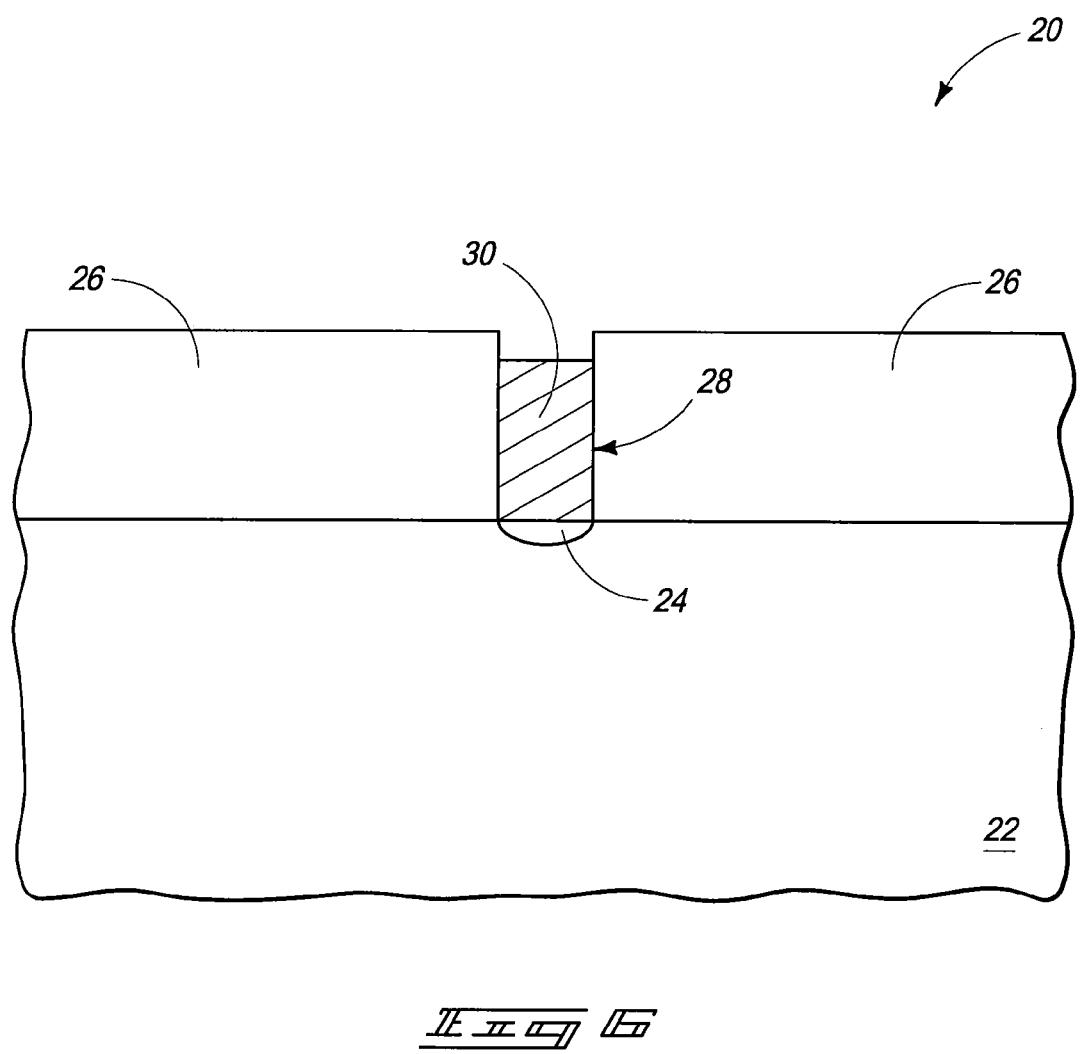
FIG. 6 is a diagrammatic sectional view of a substrate in process in accordance with an embodiment of the invention.

Embodiments of the invention also encompass methods of forming phase change memory circuitry, for example as shown and described next with reference to FIGS. 6-8. Referring to FIG. 6, such depicts a substrate fragment 20 comprising a semiconductor substrate 22, for example monocrystalline silicon. A conductively doped diffusion region 24 has been formed within semiconductor material of semiconductor substrate 22. A suitable dielectric 26 has been formed thereover, and an opening 28 formed there-through to diffusion region 24. Example dielectric materials include silicon dioxide and/or silicon nitride, whether doped or undoped.

Conductive inner electrode material 30 has been formed within opening 28 and in conductive electrical connection with diffusion region 24. Inner electrode material 30 may or may not be homogenous, with tungsten and titanium nitride being example conductive materials.

Figure 7:
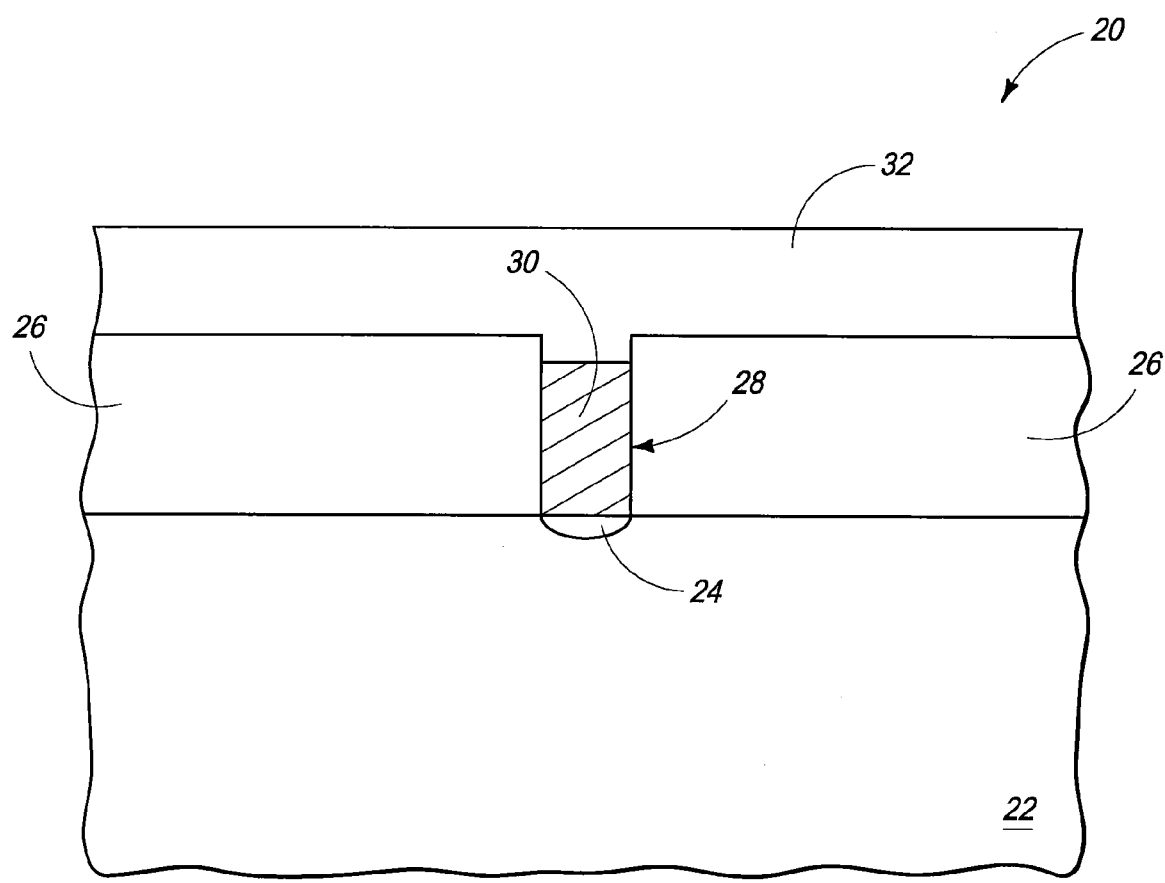
FIG. 7 is a view of the FIG. 6 substrate at a processing step subsequent to that shown by FIG. 6.

Referring to FIG. 7, a tellurium-comprising phase change material 32 has been deposited/formed over inner electrode material 30. Such may be formed by any of the techniques described above in connection with the first-described embodiments of FIGS. 1-5 in the formation of phase change material 14, and accordingly may be of the same composition (s) as material 14.

Figure 8:
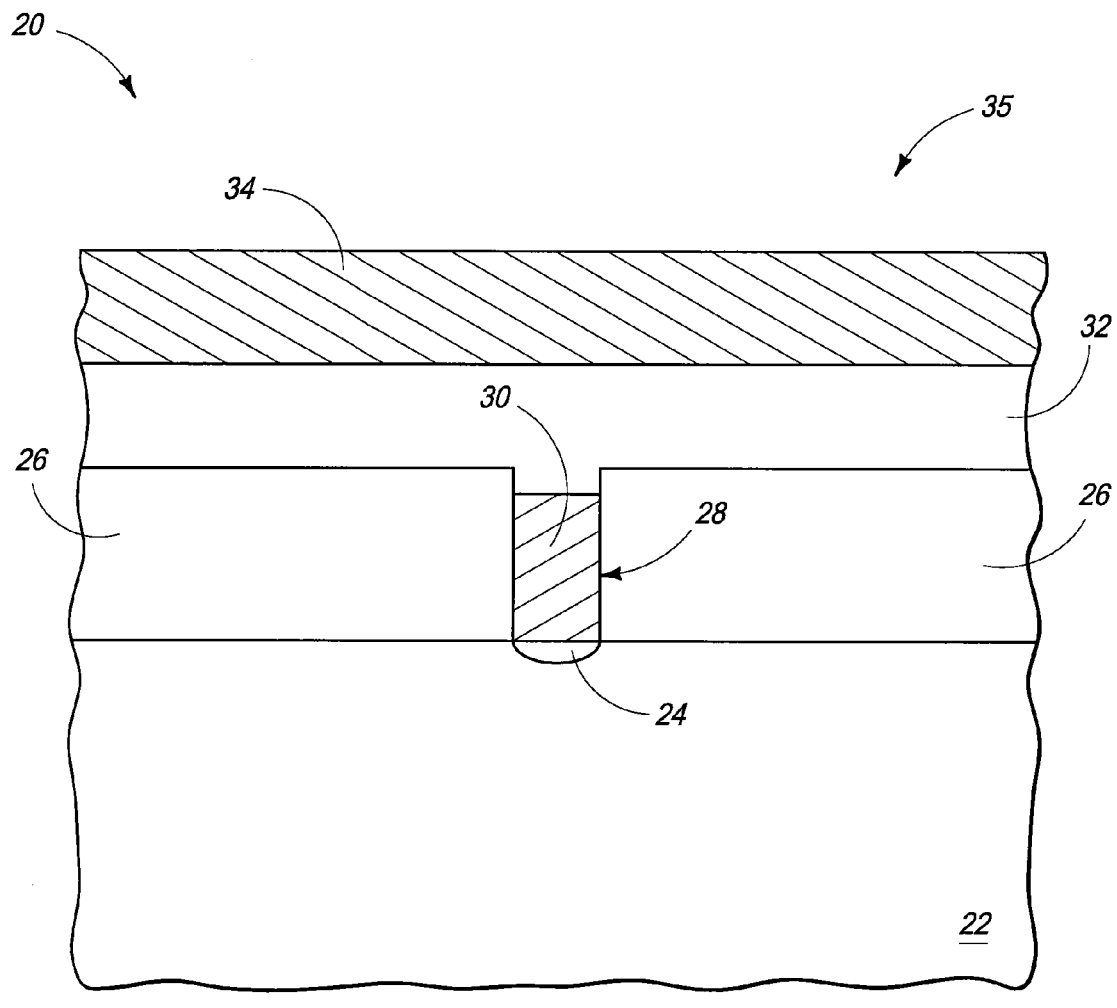
FIG. 8 is a view of the FIG. 7 substrate at a processing step subsequent to that shown by FIG. 7.

Referring to FIG. 8, outer electrode material 34 has been formed over tellurium-comprising phase change material 32, thus forming a phase change memory cell 35. Outer electrode material 34 may be the same as or different from composition of inner electrode material 30. Tellurium-comprising phase change material 32 is shown as being formed in direct physical touching contact with each of inner electrode material 30 and outer electrode material 34, although other embodiments are contemplated. The circuitry may be configured such that one or both of electrode materials 30 and 34 function as the programming electrode whereby a suitable programmable volume of tellurium-comprising phase change material 32 between inner electrode material 30 and outer electrode material 34 is switchable between high and low resistance programming states by application of suitable currents, as in existing or yet-to-be developed technology.

Figure 9:
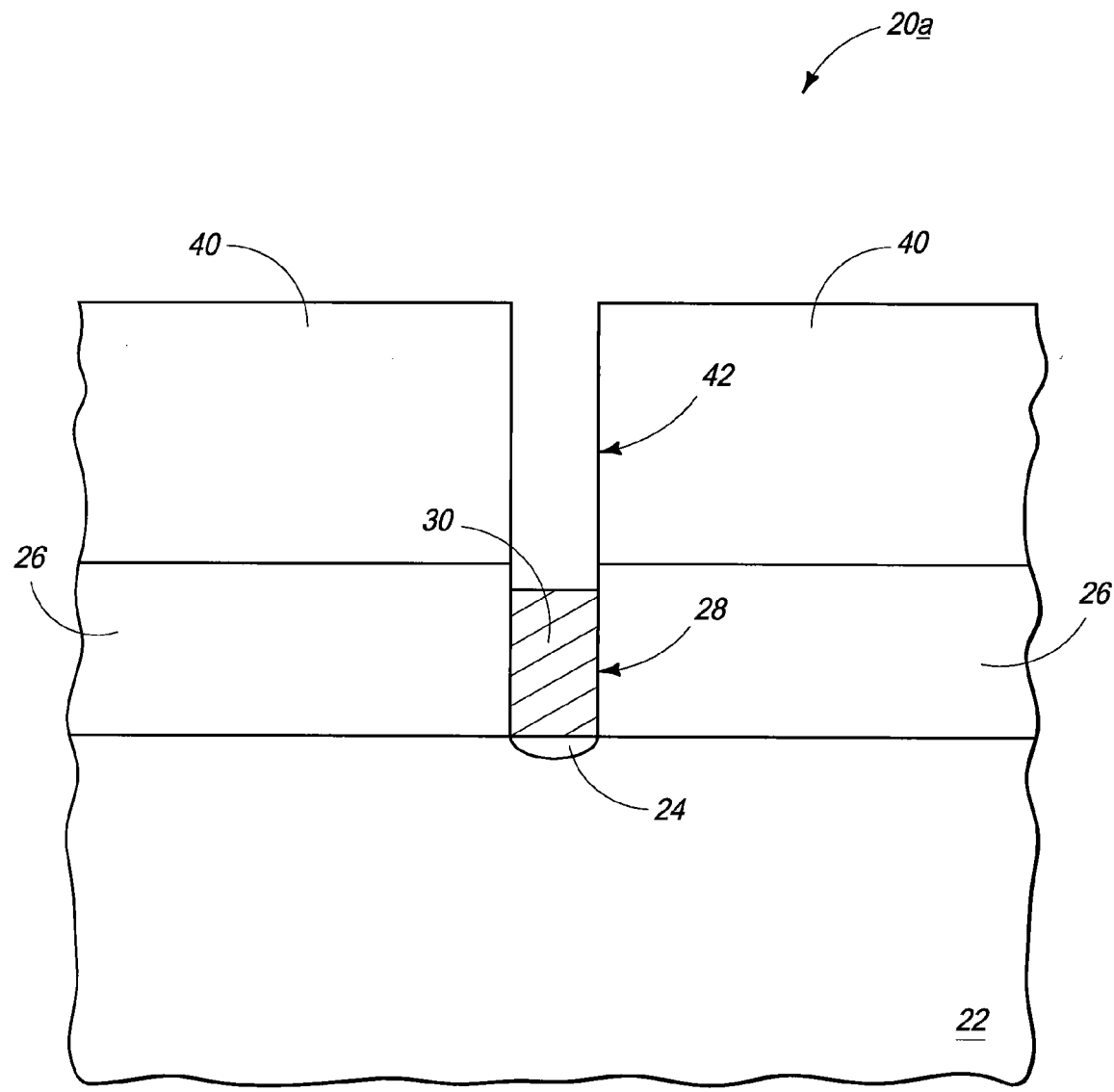
FIG. 9 is a diagrammatic sectional view of a substrate in process in accordance with an embodiment of the invention.

Additional example embodiments of forming phase change material and phase change memory circuitry are next described with reference to FIGS. 9-13. Like numerals from the above-described embodiments have been utilized where appropriate, with some construction differences being indicated with the suffix "a" or with different numerals. Referring to FIG. 9, a suitable material 40, for example a dielectric, has been formed over the substrate of FIG. 6, and which is designated as substrate 20*a* in FIG. 9. Material 40 may be the same or different in composition as that of material 26. An opening 42 has been formed therein to inner electrode material 30. Such provides but one example of forming an opening into material of a substrate wherein an inner electrode material is provided proximate a base of such opening. Any alternate construction is of course contemplated.

Figure 10:
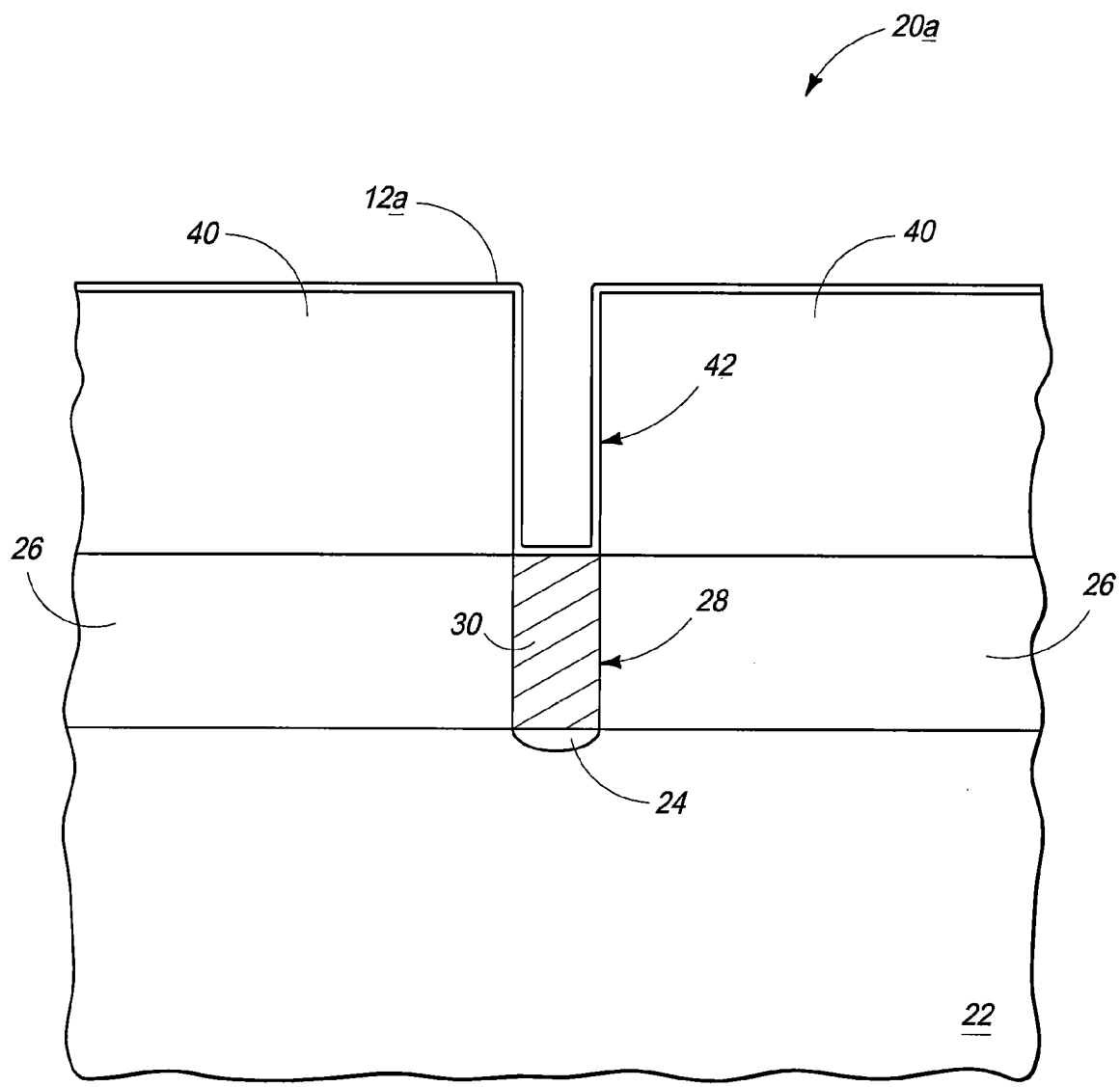
FIG. 10 is a view of the FIG. 9 substrate at a processing step subsequent to that shown by FIG. 9.

Referring to FIG. 10, opening 42 has been lined with a germanium-comprising material 12*a* which is also received over material 40 outside of opening 42. Germanium-comprising material 12*a* comprises elemental-form germanium as described above in connection with material 12 of FIG. 2. Example thickness ranges and methods of deposition include those described above.

Figure 11:
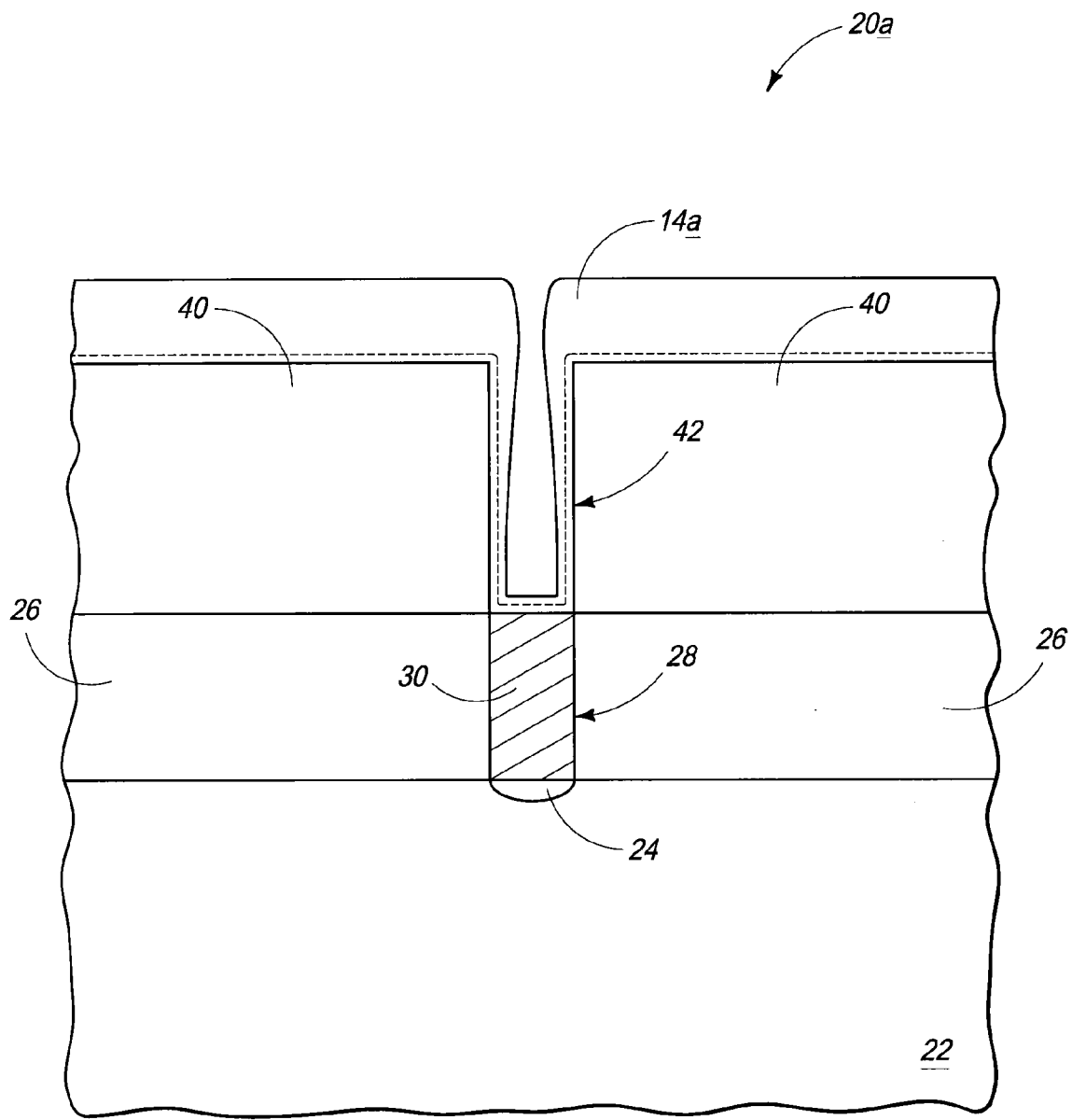
FIG. 11 is a view of the FIG. 10 substrate at a processing step subsequent to that shown by FIG. 10.

Referring to FIG. 11, a gaseous tellurium-comprising precursor has been flowed to the germanium-comprising material of FIG. 10 within opening 42 and outside of opening 42. Tellurium has been removed from the gaseous precursor to react with the elemental-form germanium in material 12*a* to form a germanium and tellurium-comprising compound of a tellurium-comprising phase change material 14*a*. Composition of material 14*a* may be the same as that described above for material 14. Rate of formation of the germanium and tellurium-comprising compound is less proximate the base of opening 42 as compared to outside of opening 42. The dashed line in FIG. 11 shows the outermost extent of germanium-comprising material 12*a* of FIG. 10. As is apparent from the FIG. 11 example, thickness of phase change material 14*a* deeper within opening 42 is less as compared to higher within opening 42 and outwardly thereof due to different rate of formation at least outwardly of opening 42 as compared to deeper within opening 42. Rate of formation of the germanium and tellurium-comprising compound may or may not be uniform deeper within opening 42, and may form thicker than shown at lower portions of opening 42 as compared to intermediate portions of opening 42.

Figure 12:
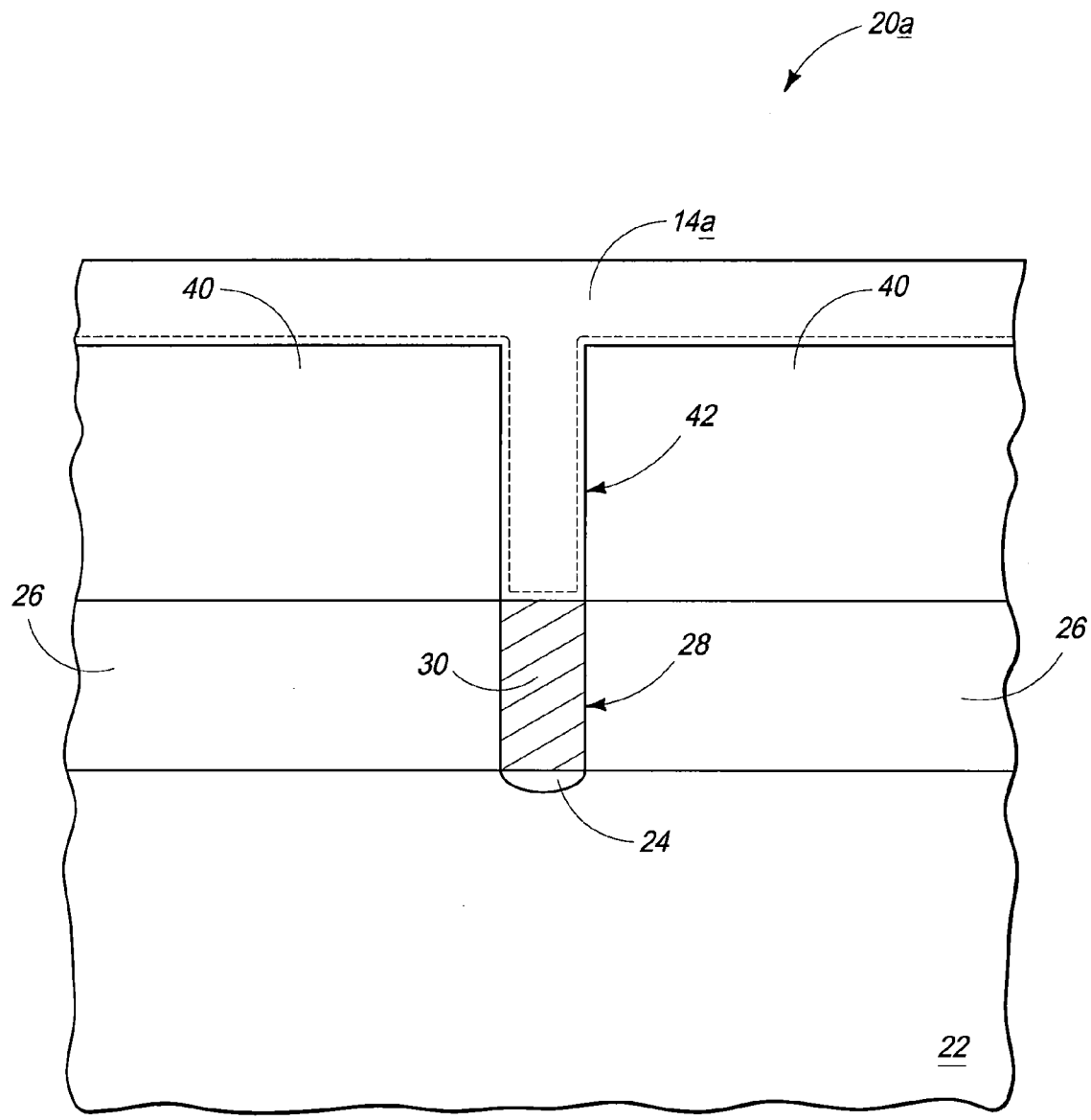
FIG. 12 is a view of the FIG. 11 substrate at a processing step subsequent to that shown by FIG. 11.

Referring to FIG. 12, flowing of the gaseous tellurium-comprising precursor has been continued beyond a point where no more of the compound is formed outside of opening 42 but has continued to be formed within opening 42 whereby the forming of the germanium and tellurium-comprising compound self-limits in thickness, for example outwardly and inwardly of opening 42. An example resultant phase change material 14*a* of substantial uniform thickness is shown in FIG. 12. Composition and processing to produce phase change material 14*a* may be as described in the above embodiments. Processing may comprise one or a combination of CVD and ALD.

Figure 13:
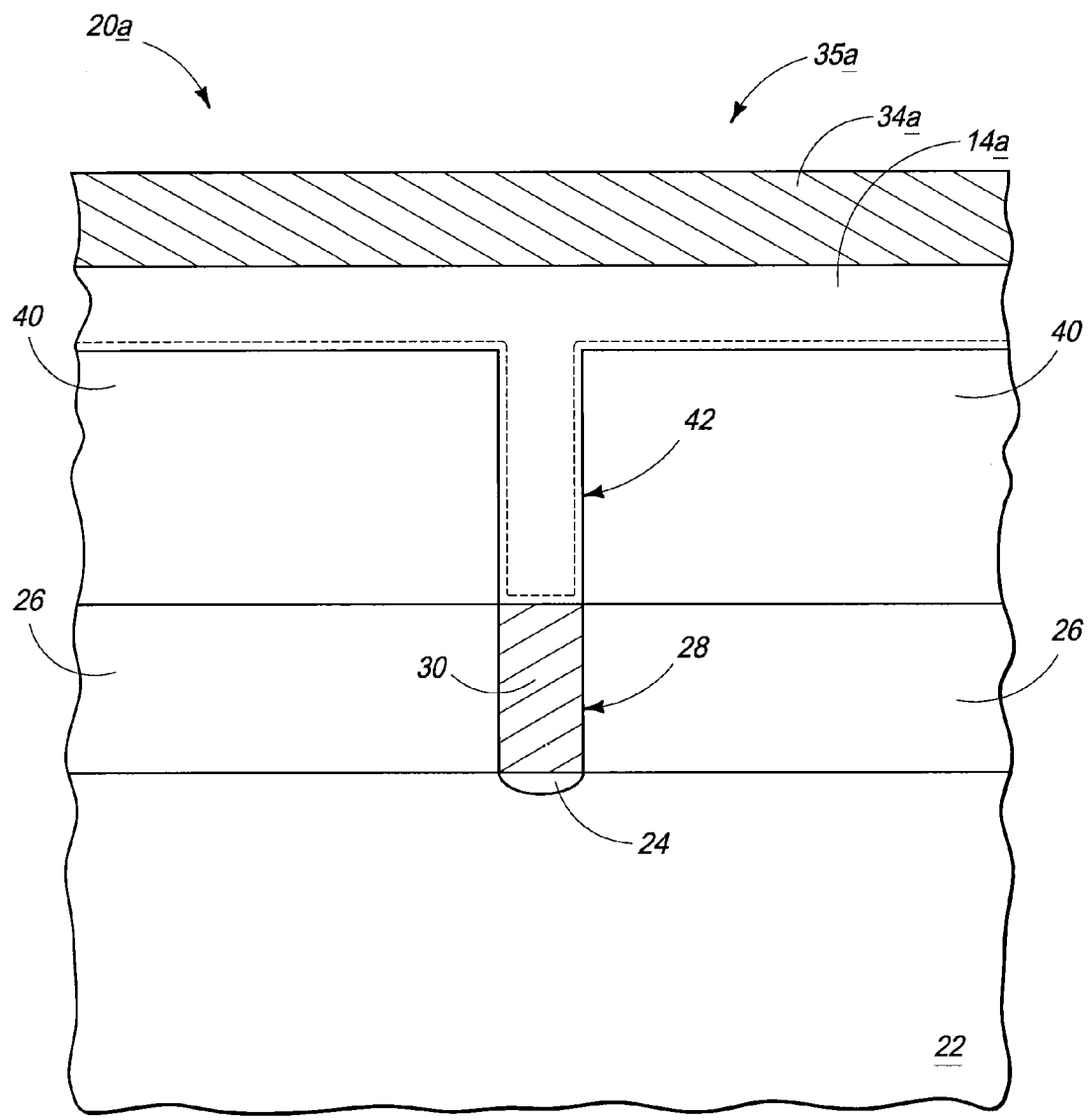
FIG. 13 is a view of the FIG. 12 substrate at a processing step subsequent to that shown by FIG. 12.

Referring to FIG. 13, outer electrode material 34*a* has been formed over tellurium-comprising phase change material 14*a*, thus forming a phase change memory cell 35*a*. Further and regardless, a phase change material may be formed within an opening, for example material 14*a* in opening 42, independent of fabrication of phase change memory circuitry.

An example ALD method is next described with reference to FIGS. 14-17. ALD involves formation of successive atomic layers on a substrate. Such layers may comprise an epitaxial, polycrystalline, amorphous, etc. material. ALD may also be referred to as atomic layer epitaxy, atomic layer processing, etc. Described in summary, ALD includes exposing an initial substrate to a first chemical specie to accomplish chemisorption of the specie onto the substrate. Theoretically, the chemisorption forms a monolayer that is uniformly one atom or molecule thick on the entire exposed initial substrate. In other words, a saturated monolayer is formed. Practically, as further described below, chemisorption might not occur on all portions of the substrate. Nevertheless, such an imperfect monolayer is still a monolayer in the context of this document. In many applications, merely a substantially saturated monolayer may be suitable. A substantially saturated monolayer is one that will still yield a deposited layer exhibiting the quality and/or properties desired for such layer.

The first specie is purged from over the substrate and a second chemical specie is provided to react with the first monolayer of the first specie. The second specie is then purged and the steps are repeated with exposure of the second specie monolayer to the first specie. In some cases, the two monolayers may be of the same specie. As an option, the second specie can react with the first specie, but not chemisorb additional material thereto. That is, the second specie can cleave some portion of the chemisorbed first specie, altering such monolayer without forming another monolayer thereon. Also, a third specie or more may be successively chemisorbed (or reacted) and purged just as described for the first and second species.

Purging may involve a variety of techniques including, but not limited to, contacting the substrate and/or monolayer with a purge gas and/or lowering pressure to below the deposition pressure to reduce the concentration of a specie contacting the substrate and/or chemisorbed specie. Examples of purge gases include $N_2$, Ar, He, etc. Purging may instead include contacting the substrate and/or monolayer with any substance that allows chemisorption byproducts to desorb and reduces the concentration of a contacting specie preparatory to introducing another specie. The contacting specie may be reduced to some suitable concentration or partial pressure known to those skilled in the art based on the specifications for the product of a particular deposition process.

ALD is often described as a self-limiting process, in that a finite number of sites exist on a substrate to which the first specie may form chemical bonds. The second specie might only bond to the first specie and thus may also be self-limiting. Once all of the finite number of sites on a substrate are bonded with a first specie, the first specie will often not bond to other of the first specie already bonded with the substrate. However, process conditions can be varied in ALD to promote such bonding and render ALD not self-limiting. Accordingly, ALD may also encompass a specie forming other than one monolayer at a time by stacking of a specie, forming a layer more than one atom or molecule thick.

The general technology of CVD includes a variety of more specific processes, including, but not limited to, plasma enhanced CVD and others. CVD is commonly used to form non-selectively a complete, deposited material on a substrate. One characteristic of CVD is the simultaneous presence of multiple species in the deposition chamber that react to form the deposited material. Such condition is contrasted with the purging criteria for traditional ALD wherein a substrate is contacted with a single deposition specie that chemisorbs to a substrate or reacts with a previously deposited specie. An ALD process regime may provide a simultaneously contacted plurality of species of a type or under conditions such that ALD chemisorption, rather than CVD reaction occurs. Instead of reacting together, the species may chemisorb to a substrate or previously deposited specie, providing a surface onto which subsequent species may next chemisorb or react to form a complete layer of desired material. Under most CVD conditions, deposition occurs largely independent of the composition or surface properties of an underlying substrate. By contrast, chemisorption rate in ALD might be influenced by the composition, crystalline structure, and other properties of a substrate or chemisorbed specie. Other process conditions, for example, pressure and temperature, may also influence chemisorption rate.

Figure 14:
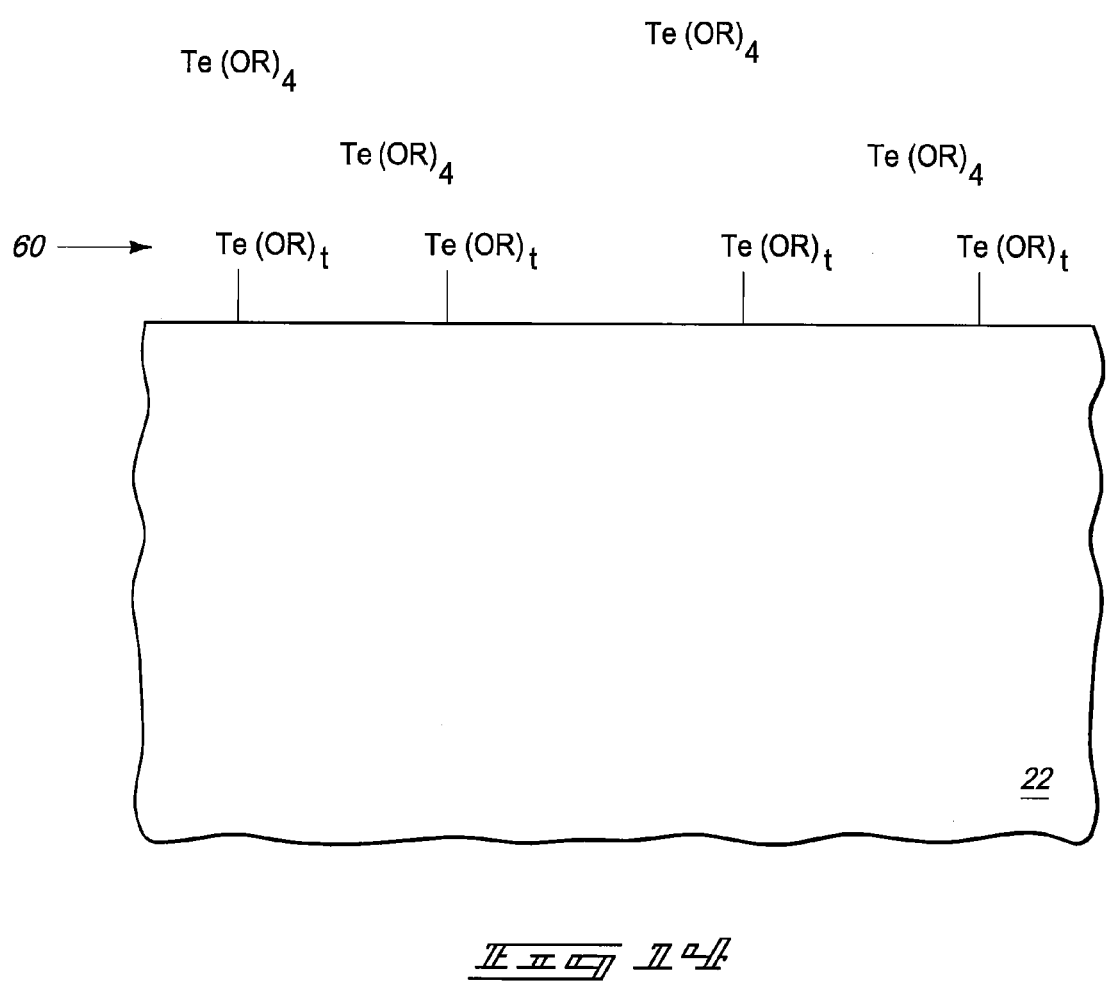
FIG. 14 is a diagrammatic sectional view of a substrate in process in accordance with an embodiment of the invention.

Referring to FIG. 14, a monolayer 60 comprising $Te(OR)_t$ has been formed onto substrate 22. Such may be formed from gaseous $Te(OR)_4$, where R is alkyl and "t" is less than 4. Example such molecules are shown over monolayer 60. Example substrate temperature and chamber pressure ranges for formation of monolayer 60 are from 100° C. to 400° C. and from 0.1 mTorr to 760 Torr. R may be any alkyl group, with methyl, ethyl, propyl, isopropyl, butyl and tert-butyl being but specific examples. Accordingly, gaseous such example precursors include tellurium methoxide, tellurium ethoxide, tellurium propoxide, tellurium isopropoxide, tellurium butoxide, tellurium isobutoxide, and tellurium tert-butoxide. Regardless, the tellurium alkoxide might be provided or flowed to the substrate from a vaporizer by flowing a carrier gas over a liquid phase of the tellurium alkoxide, sublimed from solid tellurium alkoxide, or by spraying or otherwise injecting liquid tellurium alkoxide into the chamber under pressure conditions which rapidly vaporizes the tellurium alkoxide.

Figure 15:
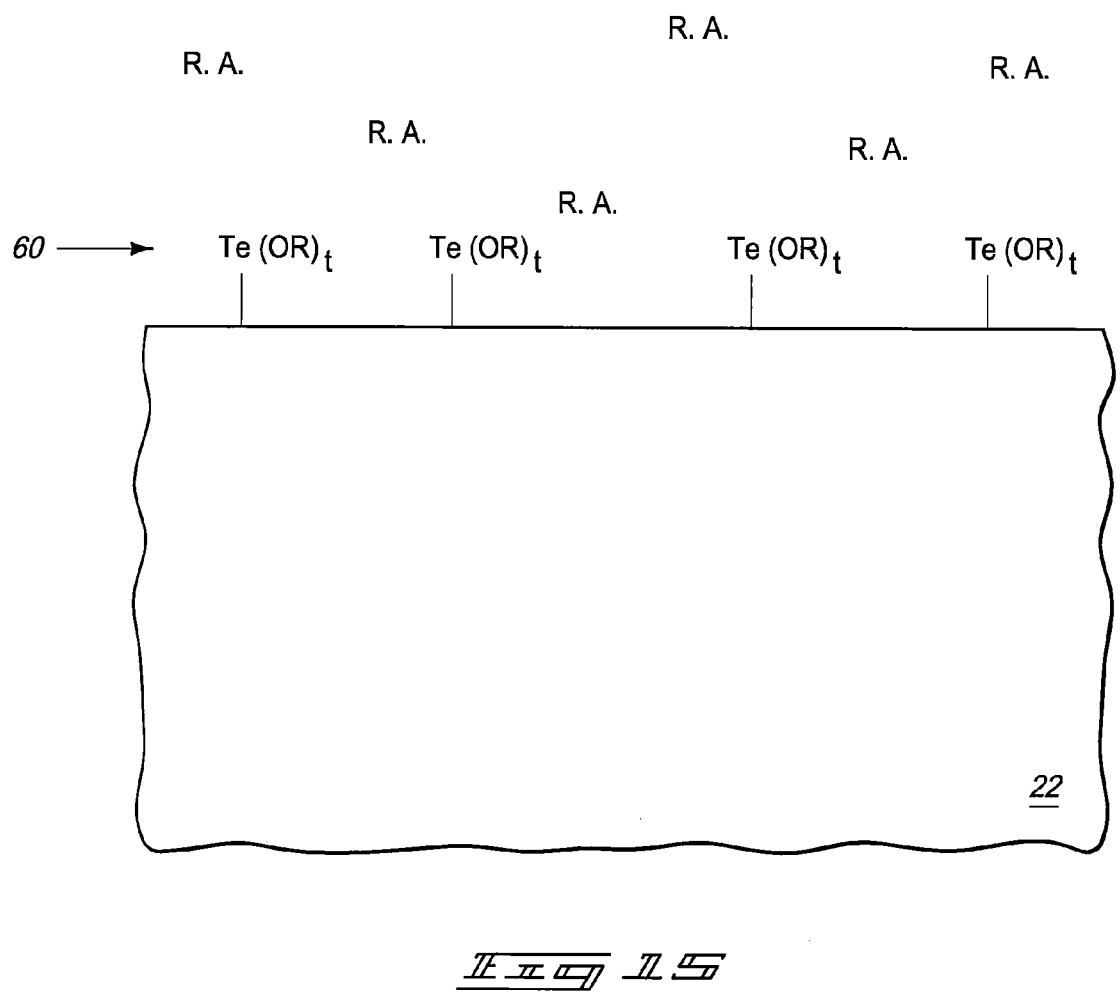
FIG. 15 is a view of the FIG. 14 substrate at a processing step subsequent to that shown by FIG. 14.
Figure 16:
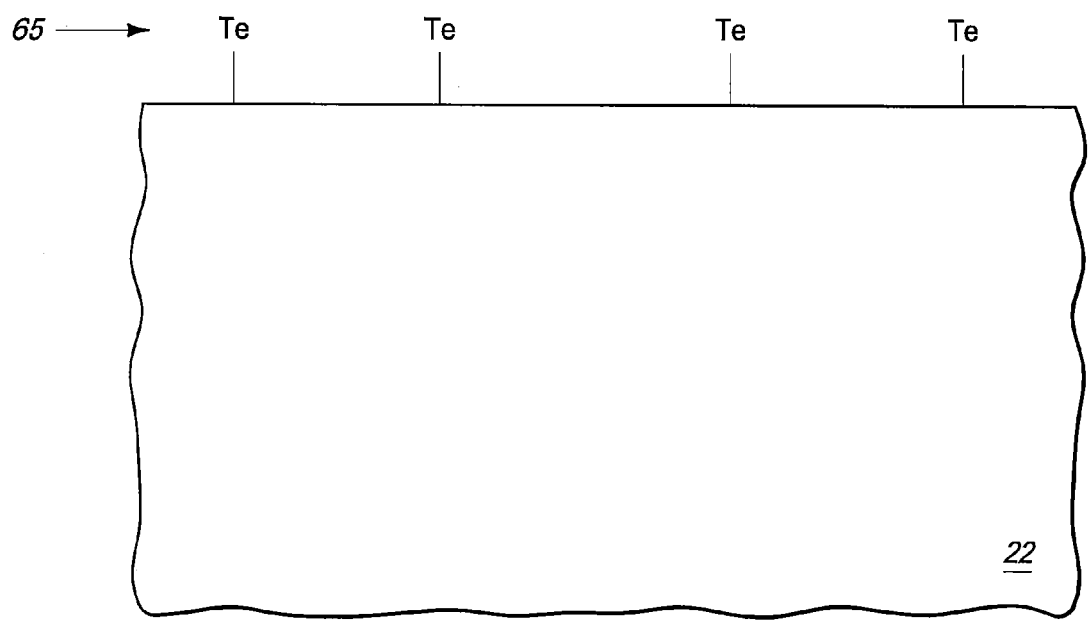
FIG. 16 is a view of the FIG. 15 substrate at a processing step subsequent to that shown by FIG. 15.

Referring to FIGS. 15 and 16, a reducing agent (R.A.) has been provided to substrate 22 having monolayer 60 formed thereover (FIG. 15) under conditions suitable to remove $(OR)_t$ ligand from the Te, thereby forming a monolayer 65 (FIG. 16). Any existing or yet-to-be developed reducing agent capable of removing at least some of the alkoxy ligands from the tellurium may be used, with $NH_3$, $H_2$, $CH_2O$, and $CH_2O_2$ being examples. Multiple of these and/or additional reducing agents may be used. Example temperature and pressure ranges are those as described above in formation of monolayer 60.

Figure 17:
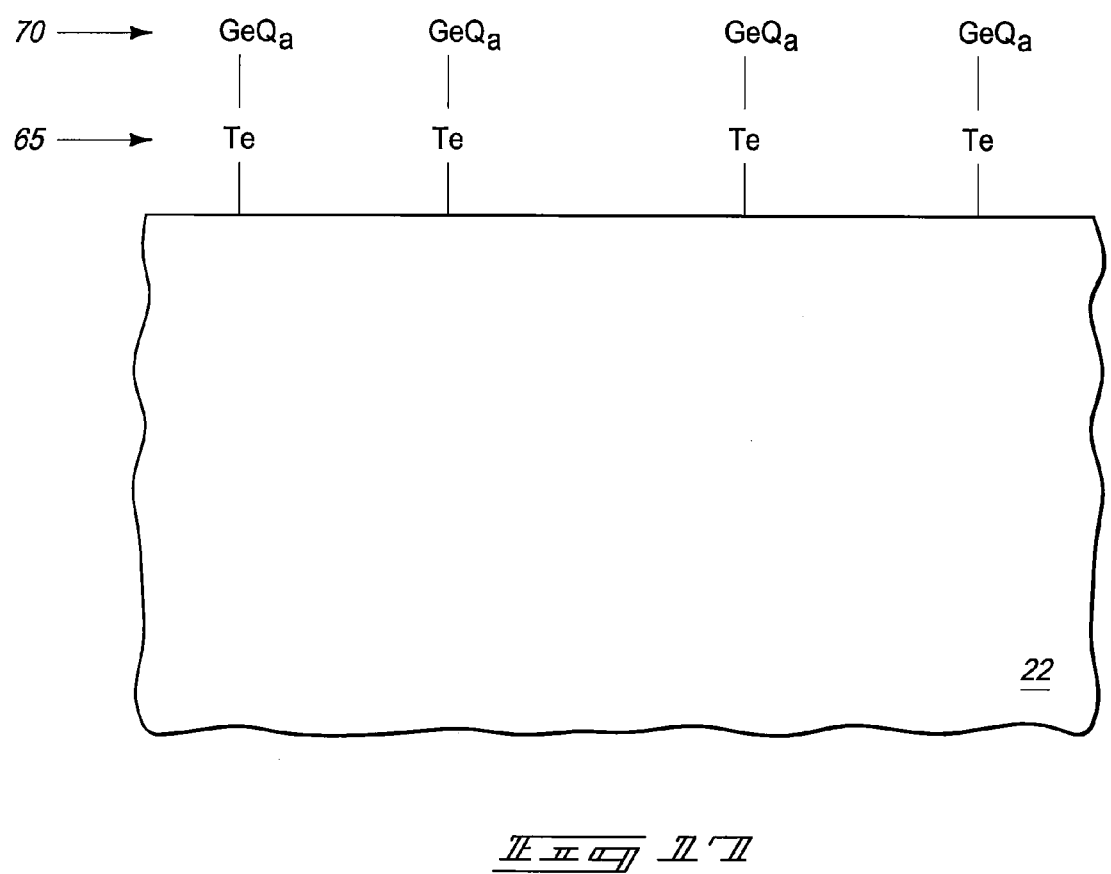
FIG. 17 is a view of the FIG. 16 substrate at a processing step subsequent to that shown by FIG. 16.

Monolayer 65 is used to form a tellurium-comprising phase change material on substrate 22, with such phase change material having no greater than 10 atomic percent oxygen and comprising another metal in additional to tellurium. In some embodiments, the phase change material which is produced has no greater than 5 atomic percent oxygen, in one embodiment no greater than 1 atomic percent oxygen, and in embodiment has no detectable oxygen therein. In some embodiments, example metals in addition to tellurium in forming a tellurium-comprising phase change material include one or both of Ge and Sb. For example, FIG. 17 depicts forming a monolayer 70 comprising $GeQ_a$ onto monolayer 65. Q may be organic or inorganic. Monolayer 70 may be formed from a suitable germanium-comprising precursor using monolayer-formation conditions as described above in connection with formation of monolayer 60 in FIG. 15. Example germanium precursors include tetrakis-dimethylamido germanium, germanium halides (i.e., $GeCl_4$), germanium hydride ($GeH_4$), tetrakis-trimethylsilyl germanium, tetra-alkyl germanes (i.e., $Ge(CH_3)_4$), and germanium amidinates [i.e., bis(N,N'-diisopropyl-N-butylamidinate) germanium II]. A suitable reducing agent such as those described above may be subsequently provided to the substrate to remove (not shown) $Q_a$ ligand. The process may be repeated to form a tellurium-comprising phase change material over substrate 22. Additional metals may be incorporated therein, for example antimony. Analogous compounds incorporating antimony instead of germanium may be used as antimony precursors to those examples described above for germanium precursors. As described above, an example germanium, antimony, and tellurium-comprising material is stoichiometric $Ge_2Sb_2Te_5$, although non-stoichiometric compositions might alternately be formed. Regardless, the tellurium-comprising phase change material which is formed using a gaseous $Te(OR)_4$ may be used in fabrication of any of the constructions described herein.

Figure 18:
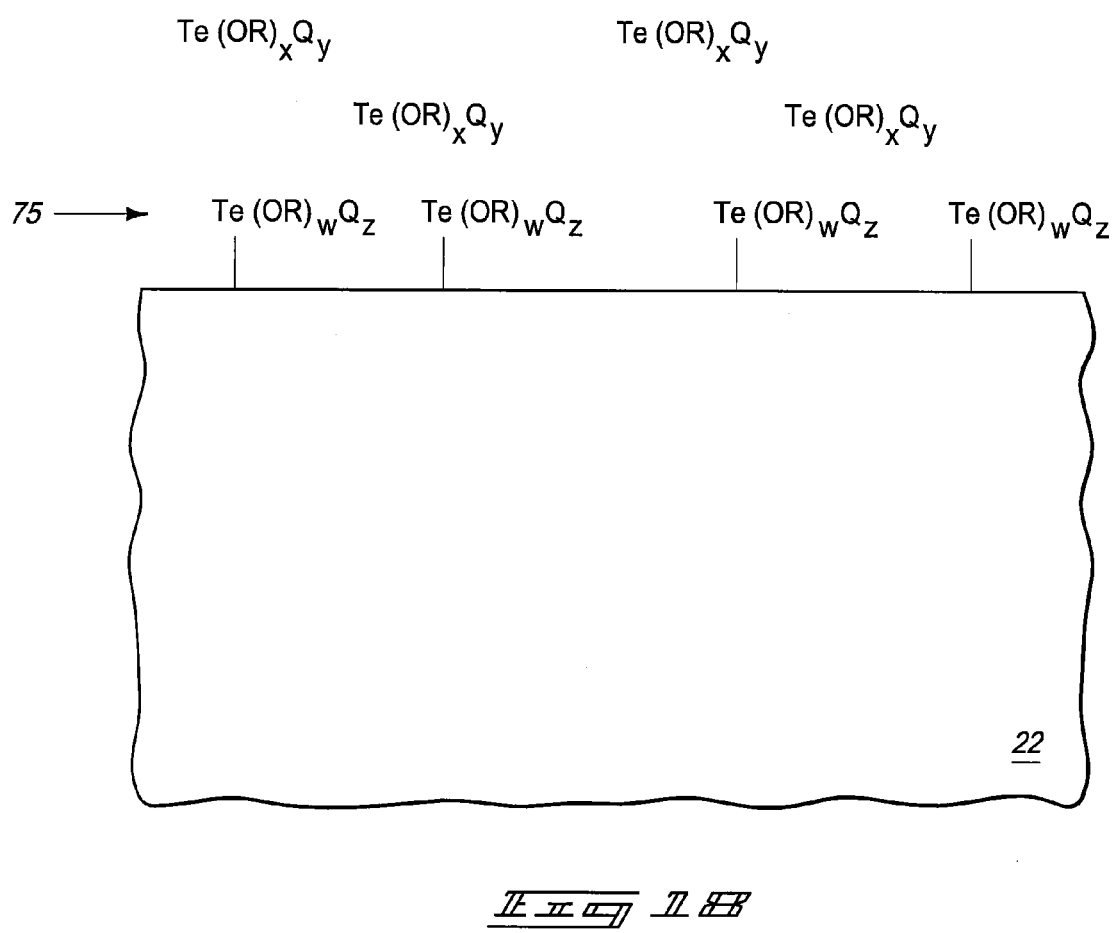
FIG. 18 is a diagrammatic sectional view of a substrate in process in accordance with an embodiment of the invention.

Another example ALD method is next described with reference to FIGS. 18-20. Referring to FIG. 18, a monolayer 75 comprising $Te(OR)_w Q_z$ has been formed onto substrate 22. Such may be formed from gaseous $Te(OR)_x Q_y$, where R is alkyl, Q is a halogen, x is less than 4, and y is 4-x. Further, at least one of w is less than x, or z is less than y. In one embodiment, both of w is less than x and z is less than y. In one embodiment, only one of w is less than x and z is less than y. Example substrate temperature and chamber pressure ranges are as described above in connection with FIG. 14. R may be any alkyl group as described above, and the $Te(OR)_x Q_y$ may also be provided or flowed to the substrate in manners as described above in connection with this description regarding FIG. 14.

Figure 19:
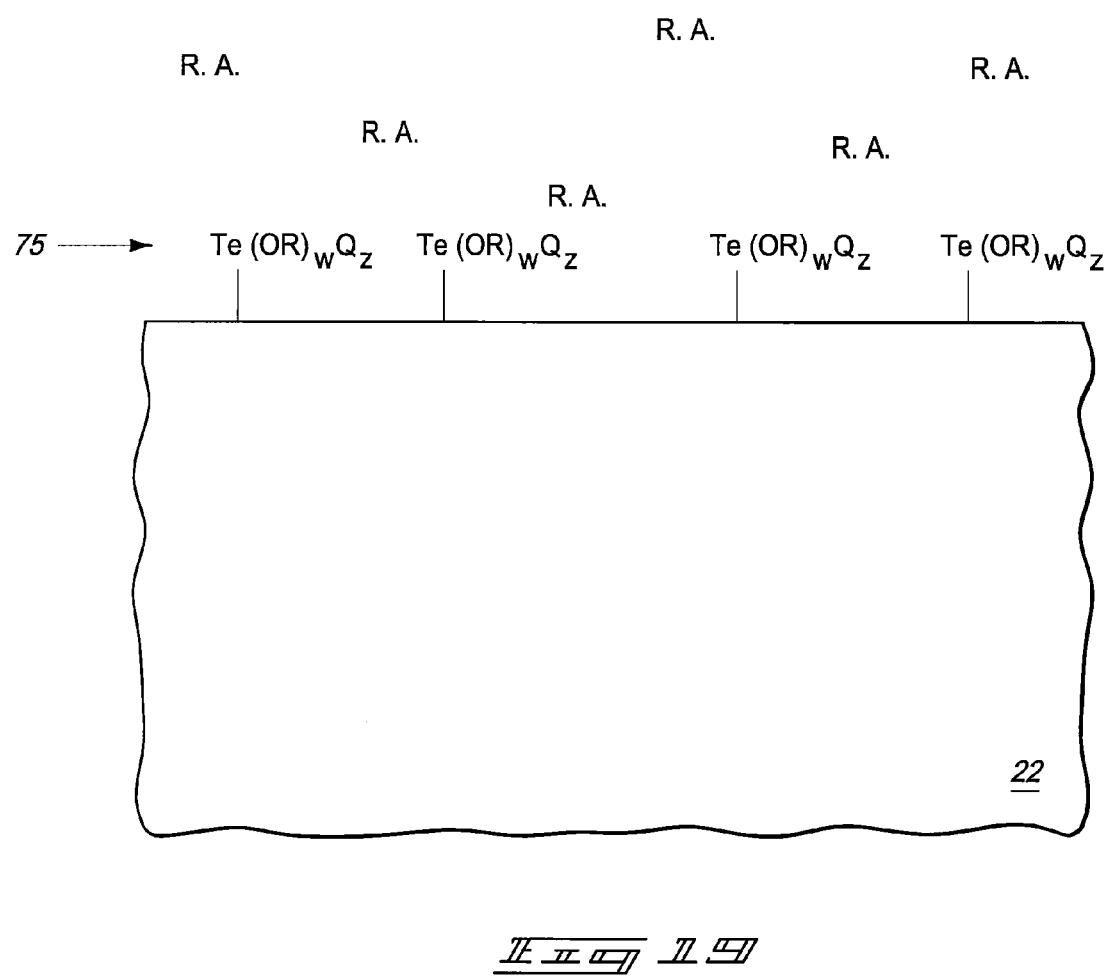
FIG. 19 is a view of the FIG. 18 substrate at a processing step subsequent to that shown by FIG. 18.
Figure 20:
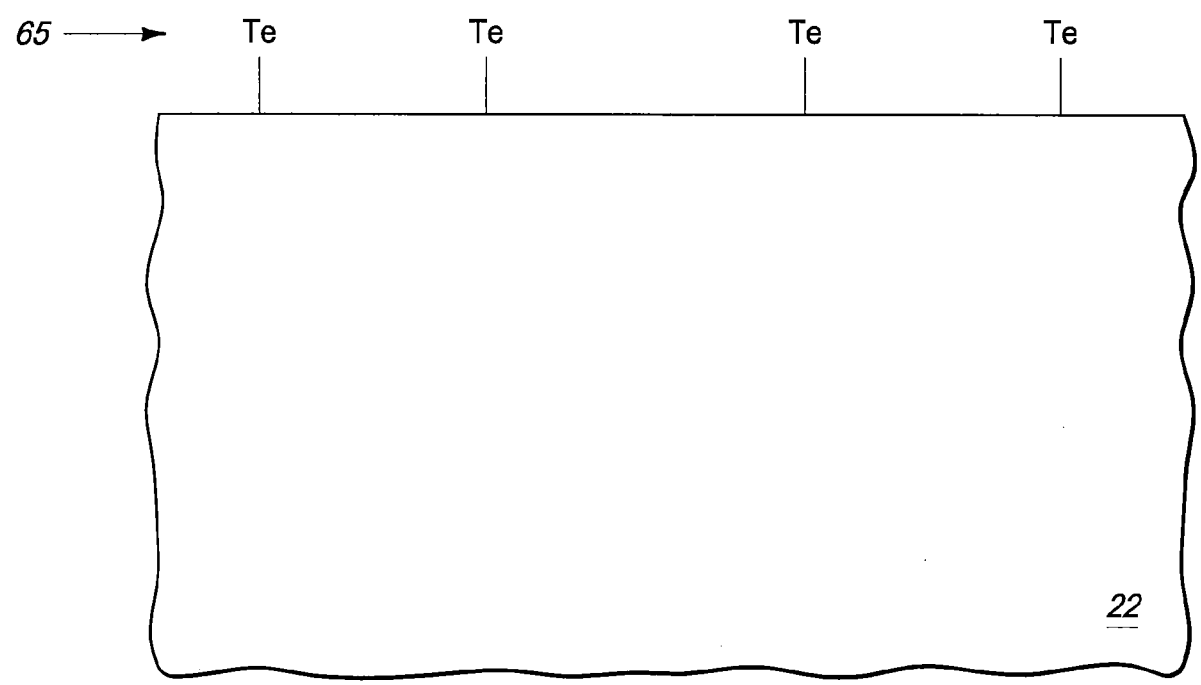
FIG. 20 is a view of the FIG. 19 substrate at a processing step subsequent to that shown by FIG. 19.

Referring to FIGS. 19 and 20, a reducing agent (R.A.) as described above has been provided to substrate 22 having monolayer 75 formed thereover (FIG. 19) under conditions suitable to remove $(OR)_w$ ligand and Q from the Te, thereby forming a monolayer 65 (FIG. 20) analogous to that formed in FIG. 16. Example temperature and pressure ranges are those as described above in formation of monolayer 75.

Monolayer 65 may be used to form a tellurium-comprising phase change material on substrate 22, for example as described above in connection with FIG. 17 and processing subsequent thereto. The phase change material has no greater than 10 atomic percent oxygen and comprises another metal in additional to tellurium, for example one or both of Ge and Sb, and/or others. In one embodiment, the phase change material which is produced has no greater than 5 atomic percent oxygen, in one embodiment no greater than 1 atomic percent oxygen, and in one embodiment has no detectable oxygen therein. The tellurium-comprising phase change material which is formed using a gaseous $Te(OR)_w Q_z$ may be used in fabrication of any of the constructions described herein.

Figure 21:
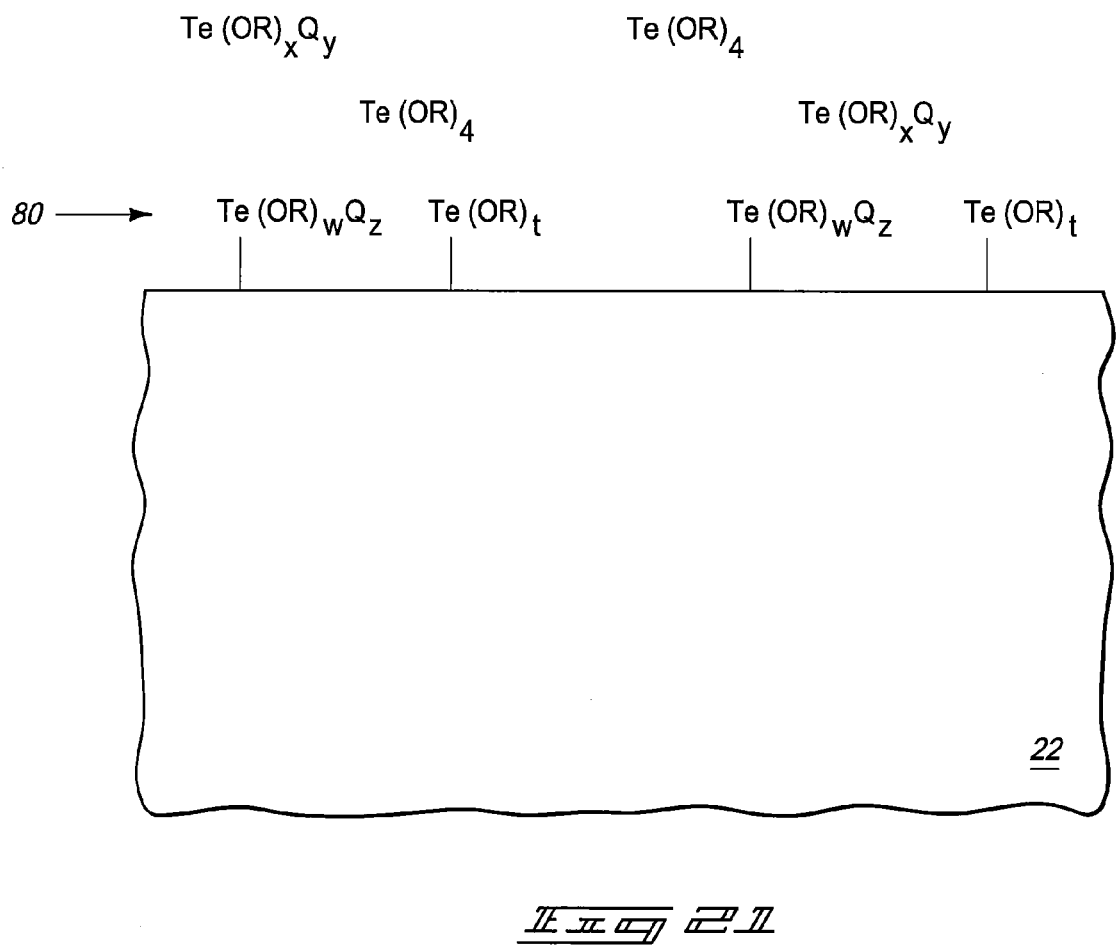
FIG. 21 is a diagrammatic sectional view of a substrate in process in accordance with an embodiment of the invention.

Another example ALD method is next described with reference to FIG. 21. A monolayer 80 has been formed onto substrate 22 which comprises both $Te(OR)_w Q_z$ and $Te(OR)_t$. Such may be formed from using a combination of gaseous $Te(OR)_x Q_y$ and gaseous $Te(OR)_4$. Processing may otherwise or additionally occur as described above in connection with FIGS. 18-20 which may be used in fabrication of any of the constructions described herein.

Tellurium alkoxides and mixed halide-alkoxides of tellurium may be obtained or manufactured by any existing or yet-to-be developed methods. Regardless, example inventive methods of forming a tellurium alkoxide or mixed halide-alkoxide of tellurium are next-described. Such encompass providing a tellurium halide and a non-tellurium alkoxide within a liquid organic solvent. Example tellurium halides include $TeCl_4$, $TeF_4$, and $TeBr_4$. Example non-tellurium alkoxides include sodium alkoxide and potassium alkoxide, for example NaOR or KOR, where R is alkyl. By ways of example only, the non-tellurium alkoxide may comprise at least one of a methoxide, and ethoxide, and tert-butoxide. Mixtures of one or more different composition tellurium halides and/or one or more non-tellurium alkoxides may be used.

The liquid organic solvent may consist of, or consist essentially of, a single organic solvent compound, or may comprise a mixture of two or more different composition organic solvent compounds. In one embodiment, the liquid organic solvent comprises a mixture comprising a polar organic solvent and a non-polar organic solvent, for example a non-polar aliphatic organic solvent. Example polar organic solvents include at least one of a toluene, an ether, tetrahydrofuran, dimethyl sulfoxide, and acetonitrile. Example non-polar liquid organic solvents include at least one of a non-polar pentane and a non-polar hexane. In one embodiment where the liquid organic solvent comprises a mixture of polar and non-polar organic solvents, an example ratio range by volume of polar organic solvent to non-polar organic solvent is from 1:1 to 20:1.

Ideally, the liquid organic solvent is void of detectable alcohol, the absence of which may facilitate formation of the tellurium alkoxide as described below. However, if any alcohol is present, the liquid organic solvent will comprise less moles of alcohol than moles of tellurium halide in the liquid organic solvent. In one embodiment, the liquid organic solvent comprises no greater than 50% moles of alcohol, if any, than moles of tellurium halide in the liquid organic solvent, and in another embodiment comprises no greater than 10% moles of alcohol, if any, than moles of tellurium halide in the liquid organic solvent.

A reaction mixture comprising a tellurium halide, a non-tellurium alkoxide, and a liquid organic solvent may be prepared in any suitable manner. For example, one or a mixture of solid tellurium halide and solid non-tellurium alkoxide may be added together or separately to a suitable liquid organic solvent. Alternately by way of example, solid tellurium halide and solid non-tellurium alkoxide might be separately added to a suitable liquid organic solvent. In one embodiment, a first mixture is formed which comprises tellurium halide and liquid organic solvent in the absence of non-tellurium alkoxide. A second mixture is formed which comprises non-tellurium alkoxide and liquid organic solvent in the absence of tellurium halide. The first and second mixtures are then combined together.

The tellurium halide and the non-tellurium alkoxide are reacted within the liquid organic solvent to form a reaction product halide and a tellurium alkoxide. The reaction may be represented as follows, where X is a halide, M is a metal, and R is alkyl:

$$TeX_4 + 4MOR \rightarrow 4MX + Te(OR)_4$$

An example temperature range for reaction is from −30° C. to 200° C., and an example pressure range is from atmospheric to greater than atmospheric pressure. However, alternate temperature and pressure combinations might be used. In one embodiment, the reacting occurs at room ambient temperature, and in one embodiment the reacting occurs at room ambient pressure. The reaction mixture may or may not be stirred during reacting. An example time of reaction is anywhere from 30 minutes to 24 hours. The reacting may form some of the tellurium alkoxide to be dissolved in the organic solvent and some of the tellurium alkoxide as solid precipitate. Presence of a polar organic solvent is believed to fundamentally facilitate formation of the tellurium alkoxide. Presence of a non-polar organic solvent may facilitate precipitation of the metal halide, and therefore also increase tellurium alkoxide product yield.

The tellurium halide and the non-tellurium alkoxide within the liquid organic solvent may react to form a mixed halide-alkoxide of tellurium. Accordingly in one embodiment, both tellurium alkoxide and a mixed halide-alkoxide of tellurium may be formed. Alternately, only one of a tellurium alkoxide or a mixed halide-alkoxide of tellurium may be formed. Such may be controlled or determined by starting molar quantity of the respective reactants. For example, where the reaction mixture includes three moles of the non-tellurium alkoxide to one mole of tellurium halide, the predominant reaction product will be a mixed halide-alkoxide of tellurium. Alternately, provision of four moles of the non-tellurium alkoxide for every one mole of the tellurium halide will predominantly produce a tellurium alkoxide which is void of halogen (i.e., pursuant to the above reaction equation. Regardless, the produced product at this point may include a combination of liquid and solid forms of each of the reaction product halide, tellurium alkoxide, and mixed halide-alkoxide of tellurium.

The liquid organic solvent is removed from the reaction product halide and from one or both of the tellurium alkoxide and/or mixed halide-alkoxide of tellurium to leave a liquid and/or solid mixture which comprises the reaction product halide and the tellurium alkoxide and/or mixed halide-alkoxide of tellurium. Such is ideally conducted by simply vaporizing the liquid organic solvent away. Such may be conducted, for example, by reducing pressure of the finished reacted mixture to a pressure of from 0.1 mTorr to 380 Torr. The mixture which comprises the reaction product halide and the tellurium alkoxide and/or mixed halide-alkoxide of tellurium may be one or a combination of solid and liquid.

The resultant mixture is heated effective to gasify the tellurium alkoxide and/or mixed halide-alkoxide of tellurium from the reaction product halide. If solid, the gasification will be via sublimation. If liquid, the gasification will be via vaporization. If both liquid and gas, a combination of sublimation and vaporization may be used. Further and regardless, a resultant product from the mixture may be solid that may be liquified or provided in an ampoule for ultimate gasification or injection to an example substrate 22 as described above.

Synthesis of tetrakis (tert.butoxy) tellurium

A one liter Schlenk flask, provided within an argon-purged glove box, was filled with 20 g (0.0745 mole) of $TeCl_4$. To this was added 125 mL of dry toluene and 100 mL of dry hexanes. A second Schlenk flask was filled with 30 g (0.31 mole) of sodium tert-butoxide suspended in 150 mL of dry hexanes. Both flasks were removed from the dry box and connected to a Schlenk line. Using a Teflon cannula, the sodium tert-butoxide suspension was added to the flask containing the $TeCl_4$ (the reaction flask) within a few minutes, while the reaction flask was cooled with ice/water. After the addition was finished, the cooling was continued for about another 15 minutes at which point the ice/water bath was removed and the reaction flask was allowed to reach room temperature. The reaction mixture was stirred for a few hours and had a slightly yellow, sand-like, color. All of the solvents were removed in vacuo and the remaining solids were transferred into a sublimator. With the temperature at about 85° C. and pressure at about 250 mTorr, a white crystalline product was isolated. (17.6 g, 56% yield. Te(theor.)=30.3%, Te(found)=30.9%, <135 ppm of chloride were found).

Synthesis of tetrakis(methoxy) tellurium

Under inert atmosphere, a one liter Schlenk flask was filled with 30 g (0.111 mole) of TeCl$_4$. To this was added about 150 mL of dry diethyl ether and about 150 mL of dry pentane, whereby the reaction mixture appeared yellow in color. A second Schlenk flask was filled with 24 g (0.444 mole) of sodium methoxide suspended in about 100 mL of dry ether and about 100 mL of dry pentane. Both flasks were connected to a Schlenk line and the flask containing the TeCl$_4$ (the reaction flask) was cooled to 0° C. using an ice/water bath. The sodium methoxide suspension was transferred to the flask with the TeCl$_4$ using a Teflon cannula. Upon completing the addition, the reaction flask was cooled for about another 30 minutes, after which it was allowed to reach room temperature. The reaction mixture was then colorless, and a white precipitate was present. After stirring for a few hours, all of the solvents were removed in vacuo and the remaining solids were transferred into a sublimator. At a temperature of about 100° C. and a pressure of about 300 mTorr, a white crystalline material sublimed. (16.4 g, 59% yield, Te(theor.)=50.7%, Te(found)=48.9%, Cl was below detection limit)

Synthesis of chloro tris(methoxy) tellurium

A one liter Schlenk flask, provided within an argon-purged glove box, was filled with 30 g (0.111 mole) of TeCl$_4$ as well as 100 mL each of dry diethyl ether and dry pentane. A second flask was filled with 18 g (0.333 mole) of sodium methoxide suspended in about 75 mL each of dry diethyl ether and dry pentane. Both flasks were removed from the dry box and connected to a Schlenk line. Using a Teflon cannula, the alkoxide suspension was added to the flask containing the TeCl$_4$ (the reaction flask), which was kept at 0° C. with an ice/water bath. After the addition was completed, the reaction flask was cooled for about another 15 minutes before it was allowed to reach room temperature. After stirring overnight, the solvents were removed in vacuo and all of the remaining solids were transferred into a sublimator. At about 85° C. and about 250 mTorr, a grey-white product sublimed. (7.83 g, 31% yield, Te(theor.)=49.8%, Te(found)=49.8%, Cl(theor.)=13.8%, Cl(found)=13.3%).

In compliance with the statute, the subject matter disclosed herein has been described in language more or less specific as to structural and methodical features. It is to be understood, however, that the claims are not limited to the specific features shown and described, since the means herein disclosed comprise example embodiments. The claims are thus to be afforded full scope as literally worded, and to be appropriately interpreted in accordance with the doctrine of equivalents.

The invention claimed is:

1. A method of forming a tellurium alkoxide, comprising:
   providing a tellurium halide and a non-tellurium alkoxide in a liquid organic solvent, the liquid organic solvent comprising less moles of alcohol, if any, than moles of tellurium halide in the liquid organic solvent;
   reacting the tellurium halide and the non-tellurium alkoxide within the liquid organic solvent to form a reaction product halide and a tellurium alkoxide;
   removing the liquid organic solvent from the reaction product halide and the tellurium alkoxide to leave a liquid and/or solid mixture comprising the reaction product halide and the tellurium alkoxide; and
   heating the mixture to gasify the tellurium alkoxide from the reaction product halide.

2. The method of claim 1 wherein the removing forms a solid-comprising mixture which comprises the reaction product halide and the tellurium alkoxide, the heating comprising subliming the tellurium alkoxide from the reaction product halide.

3. The method of claim 1 wherein the removing forms a liquid comprising mixture which comprises the reaction product halide and the tellurium alkoxide, the heating comprising vaporizing the tellurium alkoxide from the reaction product halide.

4. The method of claim 1 wherein the removing forms a liquid and solid-comprising mixture which comprises the reaction product halide and the tellurium alkoxide.

5. The method of claim 1 wherein the liquid organic solvent comprises no greater than 50 % moles of alcohol, if any, than moles of tellurium halide in the liquid organic solvent.

6. The method of claim 1 wherein the liquid organic solvent comprises no greater than 10 % moles of alcohol, if any, than moles of tellurium halide in the liquid organic solvent.

7. The method of claim 1 wherein the liquid organic solvent is void of detectible alcohol.

8. The method of claim 1 wherein the liquid organic solvent comprises a mixture of different composition organic solvent compounds.

9. The method of claim 1 wherein the reacting occurs at room ambient temperature.

10. The method of claim 1 wherein the reacting occurs at room ambient pressure.

11. The method of claim 1 comprising also reacting the tellurium halide and the non-tellurium alkoxide within the liquid organic solvent to form a mixed halide-alkoxide of tellurium.

12. The method of claim 1 wherein the removing comprises vaporizing the liquid organic solvent.

13. The method of claim 1 wherein the liquid organic solvent comprises at least one of a toluene, an ether, tetrahydrofuran, dimethyl sulfoxide, and acetonitrile.

14. The method of claim 1 wherein the liquid organic solvent comprises at least one of a pentane and a hexane.

15. The method of claim 1 wherein the non-tellurim alkoxide comprises at least one of a methoxide, an ethoxide, and a tert-butoxide.

16. The method of claim 1 wherein the reacting occurs while stirring the liquid organic solvent.

17. The method of claim 1 wherein the reacting forms some of the tellurim alkoxide to be dissolved in the organic solvent and some of the tellurium alkoxide as solid precipitate.

18. The method of claim 1 wherein said providing comprises:
   forming a first mixture comprising tellurium halide and liquid organic solvent in the absence of non-tellurium alkoxide;
   forming a second mixture comprising non-tellurium alkoxide and liquid organic solvent in the absence of tellurium halide; and
   combining the first and second mixtures.

19. A method of forming a tellurium alkoxide, comprising:
   providing a tellurium halide and a non-tellurium alkoxide in a liquid organic solvent mixture; the liquid organic solvent mixture comprising less moles of alcohol, if any, than moles of tellurium halide in the liquid organic solvent mixture; the liquid organic solvent mixture comprising a polar organic solvent and a non-polar organic solvent;

reacting the tellurium halide and the non-tellurium alkoxide within the liquid organic solvent mixture to form a reaction product halide and a tellurium alkoxide;

removing the liquid organic solvent mixture from the reaction product halide and the tellurium alkoxide to leave a liquid and/or solid mixture comprising the reaction product halide and the tellurium alkoxide; and heating the liquid and/or solid mixture to gasify the tellurium alkoxide from the reaction product halide.

20. The method of claim 19 wherein the removing forms a solid-comprising mixture which comprises the reaction product halide and the tellurium alkoxide, the heating comprising subliming the tellurium alkoxide from the reaction product halide.

21. The method of claim 19 wherein the liquid organic solvent mixture in which the tellurium halide and the non-tellurium alkoxide are provided comprises from 1:1 to 20:1 by volume of polar organic solvent to non-polar organic solvent.

22. A method of forming a mixed halide-alkoxide of tellurium, comprising:

providing a tellurium halide and a non-tellurium alkoxide in a liquid organic solvent, the liquid organic solvent comprising less moles of alcohol, if any, than moles of tellurium halide in the liquid organic solvent;

reacting the tellurium halide and the non-tellurium alkoxide within the liquid organic solvent to form a reaction product halide and a mixed halide-alkoxide of tellurium;

removing the liquid organic solvent from the reaction product halide and the mixed halide-alkoxide of tellurium to leave a liquid and/or solid mixture comprising the reaction product halide and the mixed halide-alkoxide of tellurium; and heating the mixture to gasify the mixed halide-alkoxide of tellurium from the reaction product halide.

23. The method of claim 22 wherein the liquid organic solvent comprises no greater than 10 % moles of alcohol, if any, than moles of tellurium halide in the liquid organic solvent.

24. The method of claim 22 wherein the removing forms a solid-comprising mixture which comprises the reaction product halide and the tellurium alkoxide, the heating comprising subliming the tellurium alkoxide from the reaction product halide.

25. A method of forming a mixed halide-alkoxide of tellurium, comprising:

providing a tellurium halide and a non-tellurium alkoxide in a liquid organic solvent mixture; the liquid organic solvent mixture comprising less moles of alcohol, if any, than moles of tellurium halide in the liquid organic solvent mixture; the liquid organic solvent mixture comprising a polar organic solvent and a non-polar organic solvent;

reacting the tellurium halide and the non-tellurium alkoxide within the liquid organic solvent mixture to form a reaction product halide and a mixed halide-alkoxide of tellurium;

removing the liquid organic solvent mixture from the reaction product halide and the mixed halide-alkoxide of tellurium to leave a liquid and/or solid mixture comprising the reaction product halide and the mixed halide-alkoxide of tellurium; and heating the liquid and/or solid mixture to gasify the mixed halide-alkoxide of tellurium from the reaction product halide.

26. The method of claim 25 wherein the removing forms a solid-comprising mixture which comprises the reaction product halide and the tellurium alkoxide, the heating comprising subliming the tellurium alkoxide from the reaction product halide.

* * * * *

UNITED STATES PATENT AND TRADEMARK OFFICE
CERTIFICATE OF CORRECTION

PATENT NO. : 8,148,580 B2
APPLICATION NO. : 12/424411
DATED : April 3, 2012
INVENTOR(S) : Stefan Uhlenbrock It is certified that error appears in the above-identified patent and that said Letters Patent is hereby corrected as shown below:

In column 12, line 43, in Claim 15, delete "non-tellurim" and insert -- non-tellurium --, therefor.

In column 12, line 49, in Claim 17, delete "tellurim" and insert -- tellurium --, therefor.

Signed and Sealed this
Twenty-ninth Day of May, 2012

David J. Kappos
*Director of the United States Patent and Trademark Office*